US008574221B2

(12) United States Patent
Deeds

(10) Patent No.: US 8,574,221 B2
(45) Date of Patent: Nov. 5, 2013

(54) TUBULAR MEDICAL DEVICE

(75) Inventor: Andrew C. Deeds, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 258 days.

(21) Appl. No.: 13/228,783

(22) Filed: Sep. 9, 2011

(65) Prior Publication Data

US 2013/0066298 A1    Mar. 14, 2013

(51) Int. Cl.
    *A61M 25/00* (2006.01)
(52) U.S. Cl.
    USPC ............................ 604/528; 604/910; 604/523
(58) Field of Classification Search
    USPC .................................. 604/528, 523, 174, 910
    See application file for complete search history.

(56) References Cited

U.S. PATENT DOCUMENTS

| | | | |
|---|---|---|---|
| 3,399,668 A | 9/1968 | Lundgren | 128/2 |
| 3,635,223 A | 1/1972 | Klieman | 128/348 |
| 3,665,928 A | 5/1972 | Del Guercio | 128/350 R |
| 3,938,529 A | 2/1976 | Gibbons | 128/349 R |
| 4,184,497 A | 1/1980 | Kolff et al. | 131/213 A |
| 4,207,872 A | 6/1980 | Meiri et al. | 128/4 |
| 4,465,072 A | 8/1984 | Taheri | 128/348.1 |
| 4,592,341 A | 6/1986 | Omagari et al. | 128/4 |
| 4,959,057 A | 9/1990 | Lang | 604/264 |
| 5,009,659 A | 4/1991 | Hamlin et al. | 606/159 |
| 5,037,387 A | 8/1991 | Quinn et al. | 604/51 |
| 5,052,998 A | 10/1991 | Zimmon | 604/8 |
| 5,059,169 A | 10/1991 | Zilber | 604/8 |
| 5,092,348 A | 3/1992 | Dubrul et al. | 128/899 |
| 5,256,146 A | 10/1993 | Ensminger et al. | 604/104 |
| 5,336,164 A | 8/1994 | Snider et al. | 604/4 |
| 5,395,331 A | 3/1995 | O'Neill et al. | 604/96 |
| 5,454,364 A | 10/1995 | Krüger | 600/114 |
| 5,487,730 A | 1/1996 | Marcadis et al. | 604/96 |
| 5,693,014 A | 12/1997 | Abele et al. | 604/96 |
| 5,762,631 A | 6/1998 | Klein | 604/171 |
| RE35,849 E | 7/1998 | Soehendra | 604/8 |
| 5,871,475 A | 2/1999 | Frassica | 604/264 |
| 5,902,285 A | 5/1999 | Kudsk et al. | 604/270 |
| 5,984,896 A | 11/1999 | Boyd | 604/175 |
| 5,989,230 A | 11/1999 | Frassica | 604/264 |
| 6,004,302 A | 12/1999 | Brierley | 604/264 |
| 6,063,069 A | 5/2000 | Cragg et al. | 604/508 |
| 6,248,100 B1 | 6/2001 | de Toledo et al. | 604/540 |

(Continued)

FOREIGN PATENT DOCUMENTS

| | | | |
|---|---|---|---|
| WO | WO 97/43941 A1 | 11/1997 |
| WO | WO 98/33469 A1 | 8/1998 |

(Continued)

*Primary Examiner* — Kevin C Sirmons
*Assistant Examiner* — Deanna K Hall
(74) *Attorney, Agent, or Firm* — Brinks Gilson & Lione

(57) ABSTRACT

A feeding tube is configured for nasal insertion and advancement to the jejunum of a patient. The tube has a plurality of projections disposed along the surface of the distal tube portion for promoting advancement of the tube along the GI tract by peristaltic contractions. The tube includes first and second strings. The first string is aligned along the tube such that upon exertion of a pulling force on the first string, the distal end of the tube flexes in a direction of the force. The second string is aligned such that upon exertion of a pulling force on the second string, the tube is withdrawn from the GI tract responsive to the force. A snare may be provided for capturing the second string to promote withdrawal of the tube through the mouth of the patient.

20 Claims, 7 Drawing Sheets

(56) References Cited

U.S. PATENT DOCUMENTS

| | | | |
|---|---|---|---|
| 6,293,907 B1 | 9/2001 | Axon et al. | 600/114 |
| 6,293,958 B1 | 9/2001 | Berry et al. | 606/191 |
| 6,482,178 B1 | 11/2002 | Andrews et al. | 604/164.01 |
| 6,558,349 B1 | 5/2003 | Kirkman | 604/104 |
| 6,589,213 B2 | 7/2003 | Reydel | 604/175 |
| 6,663,589 B1 | 12/2003 | Halevy | 604/96.01 |
| 6,767,339 B2 | 7/2004 | Reydel | 604/175 |
| 2001/0041874 A1 | 11/2001 | Reydel | 604/266 |
| 2008/0269686 A1 | 10/2008 | Young et al. | 604/174 |

FOREIGN PATENT DOCUMENTS

| | | |
|---|---|---|
| WO | WO 99/29362 A1 | 6/1999 |
| WO | WO 00/06239 A3 | 2/2000 |
| WO | WO 00/13736 A1 | 3/2000 |
| WO | WO 00/69498 A1 | 11/2000 |

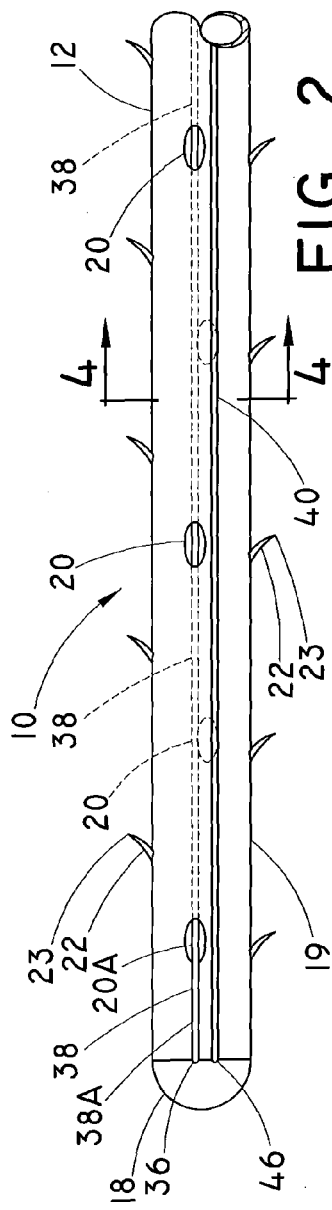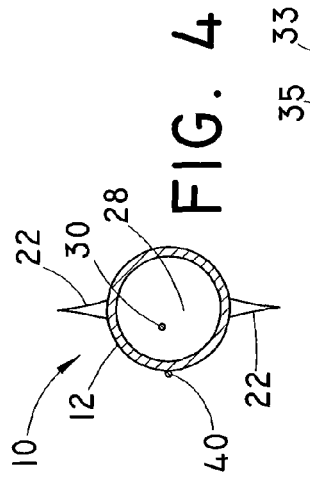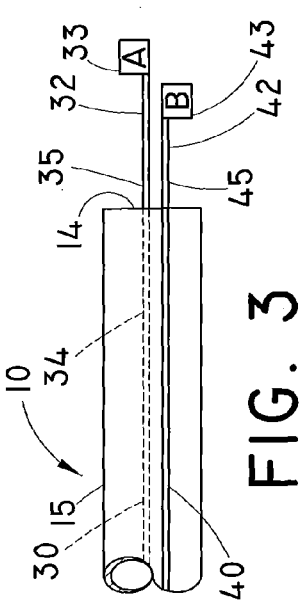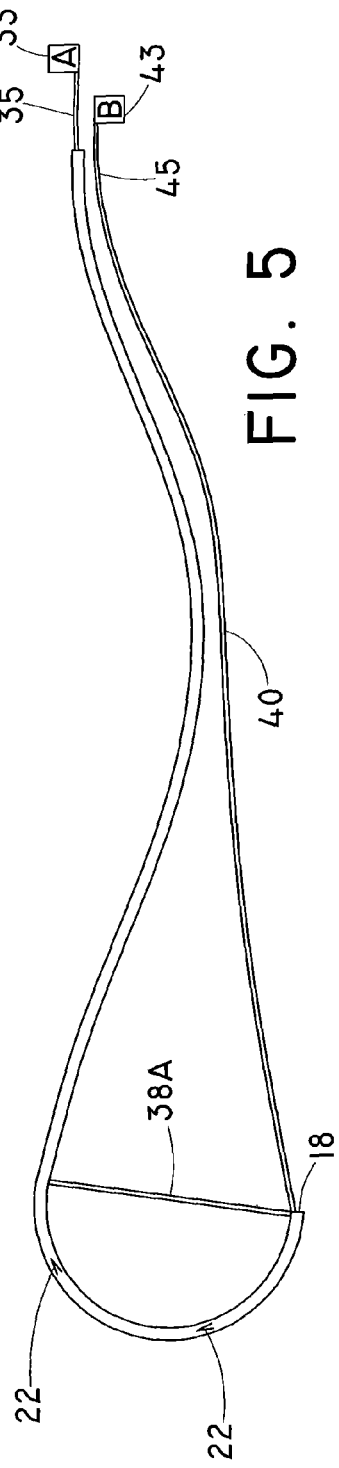

TUBULAR MEDICAL DEVICE

BACKGROUND OF THE INVENTION

1. Technical Field

The present invention relates to a tubular medical device for insertion into a patient for carrying out a medical procedure. More particularly, the invention relates to a feeding tube having a plurality of external projections along its distal length for facilitating insertion of the feeding tube through the gastrointestinal tract into the jejunum, and including a mechanism for non-traumatic removal of the feeding tube.

2. Background Information

Medical devices intended for non-destructive invasion of body passageways have typically been provided with a low friction external surface. The low friction surface has a slippery texture to facilitate ingress of the device into the body passageway for carrying out a medical procedure, and egress of the device from the body passageway following termination of the procedure. Once inserted, such low friction devices were generally suitable for their intended use. However, the devices were often difficult to deliver and properly position at the desired site. In addition, insertion required a good deal of physician time and effort to insure proper placement.

Recently, as set forth in U.S. Pat. Nos. 6,589,213 and 6,767,339, it was found that the ingress of the medical device or other instrumentation into a desired body site could be facilitated by providing certain projections on the external surface of the device that are engageable with the wall of the body passageway during ingress. The '213 and '339 patents are incorporated by reference herein in their entireties. As disclosed in the incorporated-by-reference patents, the projections are positioned along the device in a manner such that naturally occurring peristaltic contractions grasp the projections along the surface of the device upon insertion, and advance the device toward the target site. Often, such devices comprise feeding tubes for transmission of nutritional products directly into the jejunum of the patient.

When used as jejunal feeding tubes ("J-tubes") for delivering nutritional products to the jejunum, the feeding tube extends through the esophagus, and thereafter through the stomach and small intestine for delivery to the jejunum. Unlike conventional gastrostomy tubes ("G-tubes") that are utilized for delivery of nutritional products into the stomach, J-tubes bypass the stomach, and deposit the nutritional products directly into the jejunum (the middle section of the small intestine). Delivery of nutritional products to the jejunum is often preferred to delivery into the stomach, as it decreases the risk of adverse conditions such as gastric reflux and aspiration. In addition, in many cases, direct delivery into the jejunum provides better success in reaching patient nutritional targets, and does so at a more rapid rate than may be achieved with delivery into the stomach with conventional G-tubes.

The device disclosed in the '339 patent employed a series of projections positioned along the external surface of the device. The projections were positioned in a manner such that the surface of the device could be grasped by the peristaltic contractions, and the distal end of the device propelled toward the target site. Self-advancing tubes, such as those described in the '339 patent, are available commercially from Cook Medical, of Bloomington, Ind., and are sold under the trademark TIGER TUBE®. Such tubes have been well received in the medical community, and have been found to achieve a high success rate in post pyloric placement of the feeding tube.

At some point following placement of a self-advancing tube, it will become desirous to remove the tube. Such removal may be desirable, e.g., following completion of the time period within which the nutritional products have been delivered for sustenance of the patient, or when it is desired to replace the tube with another tube. A feeding tube is generally removed by simply withdrawing the tube from the passageway by pulling on the proximal end of the tube. However, the presence of radially-extending projections along the distal length of the tube may impede smooth withdrawal. Although the projections are generally relatively flexible, the presence of such projections may impose an impediment to withdrawal. In addition, some patients may experience various levels of trauma upon withdrawal due to the presence of the outwardly-extending projections.

It would be desirable to provide a tubular medical device, such as a feeding tube, having surface structure suitable for enhancing advancement of the tubular device to the target site by bodily contraction, and including a mechanism for removal of the tubular device from the body passageway with a minimum of trauma to the patient.

BRIEF SUMMARY

The present invention addresses the shortcomings of the prior art. In one form thereof, the invention comprises a medical device configured for dynamic movement through a body passageway toward an interior target site, and for withdrawal therefrom. A generally flexible elongated tubular member has a proximal portion extending to a proximal end, a distal portion extending to a distal end, a plurality of projections disposed on an exterior surface of the distal portion, a lumen extending through the tubular member, and a port at the distal portion providing communication between the lumen and an environment of the body passageway exterior of the tubular member. The projections are configured to engage an interior surface of the body passageway during bodily contractions thereof to promote ingress of the device along the body passageway in response to the contractions. A first string member has a proximal end and a distal end. The first string member extends interiorly of the tubular member along the lumen to the port, and exteriorly of the tubular member from the port substantially to the tubular member distal end. The first string member is arranged such that the proximal end extends proximal of the tubular member proximal end, and the distal end is affixed to the tubular member distal of the port. A second string member has a proximal end and a distal end, and extends exteriorly along the tubular member substantially to the distal end of the tubular member. The second string member is arranged such that the proximal end extends proximal of the tubular member proximal end, and the distal end is affixed to the tubular member distal of the port.

In another form thereof, the invention comprises a feeding tube configured for dynamic movement through the gastrointestinal tract of a patient to the jejunum, and for withdrawal therefrom. A flexible elongated tubular member has a proximal portion extending to a proximal end, a distal portion extending to a distal end, a plurality of projections disposed along an exterior surface of the distal portion, a lumen extending through the tubular member, and a port at the distal portion providing communication between the lumen and the jejunum. The projections are configured to engage an interior surface of the gastrointestinal tract during contractions thereof to promote ingress of the tubular member along the gastrointestinal tract to the jejunum in response to the contractions. A first string member has a proximal end and a distal end. The first string member extends interiorly of the tubular member along the lumen to the port, and exteriorly of the tubular member from the port to a first affixation point of the first string member distal end substantially at the tubular member distal end. The first string member proximal end extends proximal of the tubular member proximal end. The first string member is configured and arranged relative to the tubular member such that upon exertion of a pulling force on the first string member proximal end, the tubular member distal portion flexes in a direction of the force. A second string member has a proximal end and a distal end. The second string member extends exteriorly along the tubular member to a second affixation point of the second string member distal end substantially at the tubular member distal end. The second string member proximal end extends proximal of the tubular member proximal end. The second string member is arranged such that upon exertion of a pulling force on the second string member proximal end, the tubular member is withdrawn from the gastrointestinal tract responsive to the force.

In yet anotherform thereof, the invention comprises a method for insertion of a feeding tube into the jejunum of a patient, and withdrawal therefrom. The distal end of a feeding tube is inserted nasally into the gastrointestinal tract of the patient. The feeding tube has a proximal portion extending to a proximal end, a distal portion extending to the distal end, a plurality of projections disposed along an exterior surface of the distal portion, a lumen extending through the feeding tube, and a port at the distal portion. The feeding tube includes a first string member and a second string member. The first string member extends interiorly of the feeding tube along the lumen to the port, and exteriorly of the feeding tube from the port to a first affixation point substantially at the feeding tube distal end. The first string member has a proximal end extending proximal of the feeding tube proximal end. The second string member extends exteriorly along the feeding tube to a second affixation point substantially at the feeding tube distal end. The second string member has a proximal end extending proximal of the feeding tube proximal end. The feeding tube is advanced along the gastrointestinal tract by peristaltic contractions acting upon the feeding tube projections, such that the distal portion of the feeding tube advances into the jejunum. A pulling force is exerted on the proximal end of the first string member such that the feeding tube distal portion flexes in a direction of the pulling force. A pulling force is exerted on the proximal end of the second string member, and the feeding tube distal portion is withdrawn a distance along the gastrointestinal tract, such that a length of the feeding tube distal portion folds back upon a remaining length of the feeding tube. A snare is inserted orally to capture a proximal portion of the second string member. The snare and the proximal end of the second string member are withdrawn through the mouth of the patient. A pulling force is exerted on the second string member to withdraw the feeding tube through the mouth of the patient.

BRIEF DESCRIPTION OF THE DRAWINGS

FIG. 2 is a side view of the distal end of a feeding tube according to an embodiment of the present invention;

FIG. 3 is side view of the proximal end of the feeding tube of FIG. 2;

FIG. 4 is a cross-sectional view taken through line 4-4 of FIG. 2;

FIG. 5 is a side view of the feeding tube of FIGS. 2 and 3 on a smaller scale, wherein the distal end of the feeding tube has been adjusted into a withdrawal position;

DESCRIPTION OF THE PREFERRED EMBODIMENTS

Figure 1:
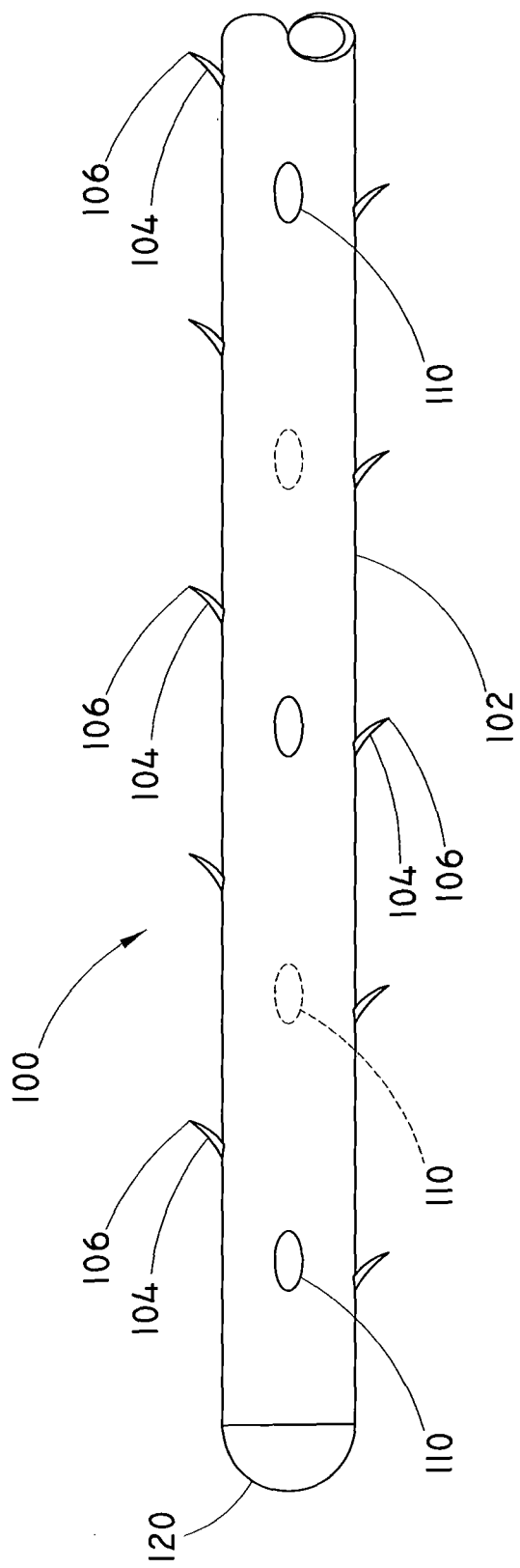
FIG. 1 is a side view of the distal end of a prior art feeding tube.

For purposes of promoting an understanding of the present invention, reference will now be made to the embodiments illustrated in the drawings, and specific language will be used to describe the same. It should nevertheless be understood that no limitation of the scope of the invention is hereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the tubular device, such as a feeding tube, as well as the axial ends of various component features of the tubular device. The term "proximal" is used in its conventional sense to refer to the end of the tubular device (or component thereof) that is closest to the operator during use of the tube. The term "distal" is used in its conventional sense to refer to the end of the tubular device (or component thereof) that is initially inserted into the patient, or that is closest to the patient during use.

FIG. 1 illustrates a side view of the distal portion of a prior art feeding tube 100. The prior art feeding tube 100 illustrated herein is a jejunal feeding tube for delivering nutritional products directly into the jejunum of a patient. Feeding tube 100 comprises an elongated tubular member 102 extending to a distal end 120. Tubular member 102 has a plurality of projections 104 extending radially from the external surface of the tubular member. In the embodiment of FIG. 1, the projections 104 are in the nature of a series of fins disposed along the outer surface of the tubular member. The fins may be formed by cutting a portion of the outer surface of the tubular member 102, and by heat shaping the fins to a desired orientation. Alternatively, the fins can be separately formed, and combined with the feeding tube by conventional means such as via heat bonding or adhesion.

In the prior art embodiment shown, the fins alternate along opposite sides of the tubular member, and are configured such that fin tips 106 are oriented to point toward the proximal end of the tubular member. The structure and orientation of fins 104 and fin tips 106 causes the feeding tube 100 to be propelled forwardly along the gastrointestinal tract by the naturally occurring peristaltic contractions of the tissue of the gastrointestinal tract during ingress of distal portion of the feeding tube into the jejunum. The orientation of the fins, and in particular the proximal (i.e., rearward) orientation of the fin tips, is intended to resist undesired movement of the tube in the opposite direction.

The prior art feeding tube of FIG. 1 further includes a lumen extending therethrough (not shown) as well as feeding tube ports, or apertures, 110 disposed along the distal portion of the catheter. The feeding tube ports may measure approximately 0.5 cm in diameter, and comprise generally circular, elliptical, etc., openings through which fluid or fluid-like material can pass from the lumen of the feeding tube into the body canal or cavity at the target site. In the prior art tube shown, the feeding tube ports 110 are alternately disposed along opposite sides of the feeding tube.

It is, of course, apparent that at some point the feeding tube will have to be withdrawn from the gastrointestinal tract. Although the fins 104 are beneficial for propelling the feeding tube forward during peristaltic contractions as described, they do not contribute in any meaningful way to the withdrawal, or egress, of the tube following termination of the period of feeding. During egress, the feeding tube is withdrawn in a direction opposite to that urged by the peristaltic contractions. At this time, any grasping or contractile effect is counterproductive to smooth removal of the tube. In addition, the additional diameter occasioned by the presence of the fins may pose an impediment to withdrawal.

FIG. 2 illustrates a side view of the distal portion of a feeding tube 10 according to an embodiment of the present invention. FIG. 3 illustrates a side view of the proximal portion of feeding tube 10. FIG. 4 illustrates a sectional view of feeding tube 10 taken along line 4-4 of FIG. 2. As with the feeding tube depicted in FIG. 1, feeding tube 10 may be a jejunal feeding tube for delivering nutritional products directly into the jejunum of a patient.

Feeding tube 10 comprises an elongated tubular member 12, having a proximal end 14 and a distal end 18. Proximal portion 15 extends in a distal direction from proximal end 14. Distal portion 19 extends in a proximal direction from distal end 18. Tubular member has sufficient flexibility to bend as described herein.

A plurality of projections 22 extend radially from the external surface of tubular member distal portion 19. The projections may be formed, e.g., by cutting a portion of the outer surface of the tubular member 12, and by heat shaping the projection to a desired configuration and orientation, as described in the incorporated-by-reference patents. The projections 22 may be in the nature of a series of fins disposed along the outer surface of the tubular member as shown in FIG. 1. Fins 22 may alternate along opposite sides of the tubular member, and extend to fin tips 23. The fins are preferably configured in a manner to orient the fin tips 23 rearwardly (i.e., pointing away from the distal end 18 of the feeding tube 10). This rearward orientation of fins 22 causes feeding tube 10 to be propelled forwardly by the naturally occurring peristaltic contractions of the tissue of the gastrointestinal tract during the insertion process (ingress). The orientation also resists unintended egress of the tube.

In one embodiment, fins 22 may be approximately 0.5 cm in length from the base of the fin (where the fin meets the tubular body) to the fin tip, and the base of the fin may be approximately 0.02 cm in width. The respective configuration and dimensions of fins 22 as described herein and as shown in FIG. 2 is only one non-limiting example of a suitable arrangement of fins, projections, or other structures capable of advancing a tubular member along a body canal by body contractions. Those skilled in the art will appreciate that other arrangements and dimensions of projections, including fins or other structures capable of advancing the tubular member responsive to bodily contractions, may be substituted for the fins 22 specifically shown and described herein.

Feeding tube 10 includes a series of ports 20 disposed along the distal portion of tubular member 12, as described previously with regard to the prior art feeding tube of FIG. 1. One of the ports, typically distal-most port 20A, is preferably disposed about 1-2 inches proximal of tubular member distal end 18. Feeding tube 10 also includes a lumen 28 extending therethrough (FIG. 4) to closed distal end 18. Lumen 28 communicates with an area exterior of feeding tube 10 through ports 20, 20A. Lumen 28 is of sufficient diameter to permit passage therethrough of fluid and fluid-like products in well-known fashion. Although distal end 18 is closed in the preferred embodiment shown and described, those skilled in the art will appreciate that, if desired, the tubular member distal end may be open to permit additional fluid flow therethrough.

Feeding tube 10 includes a first string member 30 and a second string member 40. First string member 30 includes a proximal end 32 and a distal end 36. A proximal portion 34 of the first string member extends interiorly of tubular member 12 along passageway 28 (FIG. 4) in a distal direction from proximal end 32. A segment 35 of proximal portion 34 extends proximally of tubular member proximal end 14. Segment 35 is positioned in a manner to enable the operator to grasp the proximal end 32 of the first string member. An optional tab 33 or like structure may be affixed to proximal end 32 to facilitate grasping.

A distal portion 38 of the first string member extends to distal end 36. Distal portion 38 extends interiorly of tubular member 12 along passageway 28 in a distal direction from proximal portion 34 to port 20A. A length 38A of distal portion 38 extends exteriorly of tubular member 12 from port 20A to tubular member distal end 18. First string member distal end 36 is securely affixed to tubular member 12 in the vicinity of tubular member distal end 18. This is best shown in FIG. 2. First string member distal end 36 may be affixed to the tubular member in any known manner, such as by sewing the string member end into tubular member distal end 18, or by the use of a suitable adhesive.

Second string member 40 includes a proximal end 42 and a distal end 46. Second string member 40 extends exteriorly along the length of tubular member 12 from proximal end 42 to distal end 46. As with first string member distal end 36, distal end 46 of the second tubular member is securely affixed to tubular member 12 in the vicinity of distal end 18, such as by sewing or use of a suitable adhesive. A segment 45 of proximal second string member 40 extends proximally of tubular member proximal end 14. Segment 45 is positioned to enable the operator to grasp the proximal end 42 of the second string member. An optional tab 43 or like structure may be affixed to proximal end 42 to facilitate grasping, in the same manner as tab 33 affixed to the proximal end of the first string member.

If desired, a designator may be applied to each of the tabs 33, 43 to enable the operator to readily distinguish first string member 30 and second string member 40. In the example illustrated herein, the letter "A" is applied to tab 33 to designate first string member 30, and the letter "B" is applied to tab 43 to designate second string member 30. Those skilled in the art will appreciate that numerous other well-known means may be employed to distinguish the string members, such as by varying the color and/or configuration of the string members, and/or adding one or more words, numbers, symbols, etc., of identification to the tab. As a still further alternative, the string members may be constructed in a manner such that suitable identifying indicia may be formed directly on the string member, in the absence of a discrete tab.

Jejunal feeding tubes, such as tube 10, generally have an outer diameter of about 8 to 16 French, and a length of about 150 to 160 cm. Typically, such tubes are formed of a flexible polymeric composition, such as PVC or polyurethane, or from other flexible elastomeric compositions, such as silicone. The projections, e.g., fins, are typically formed on the outer surface of approximately the distal-most 50 cm of the tubular member. In addition to the orientation as shown in the figure, the fins or other projections may be spaced and oriented along this distal length of the tubular member in any manner that is suitable for achieving ingress via the peristaltic contractions as described. Those skilled in the art will appreciate that the dimensions and compositions described hereinabove, as well as other dimensions and compositions recited herein, are exemplary only, and that other dimensions and compositions may be appropriate for a particular case.

Other than as described herein, the size, shape, and composition of feeding tube 10 may be the same or similar as found in existing feeding tubes, such as prior art feeding tube 100. Additional description and discussion of such feeding tubes is provided in the incorporated-by-reference U.S. Pat. Nos. 6,589,213 and 6,767,339, cited above.

The following discussion describes use of tube 10, in particular, with regard to insertion of the distal end of the tube into the jejunum (ingress), and withdrawal of the tube (egress). In this example, the distal end of feeding tube 10 is initially inserted into the patient nasally, and is directed into the gastrointestinal tract in well-known fashion. Peristalsis acts on the tube in the GI tract, and most particularly, on the fins 22 disposed along the distal portion of tubular member 12. As stated, fins 22 are positioned along the surface of the device in a manner such that the naturally occurring peristaltic contractions grasp the fins upon insertion, and carry the distal end of the feeding tube into the jejunum.

Figure 6:
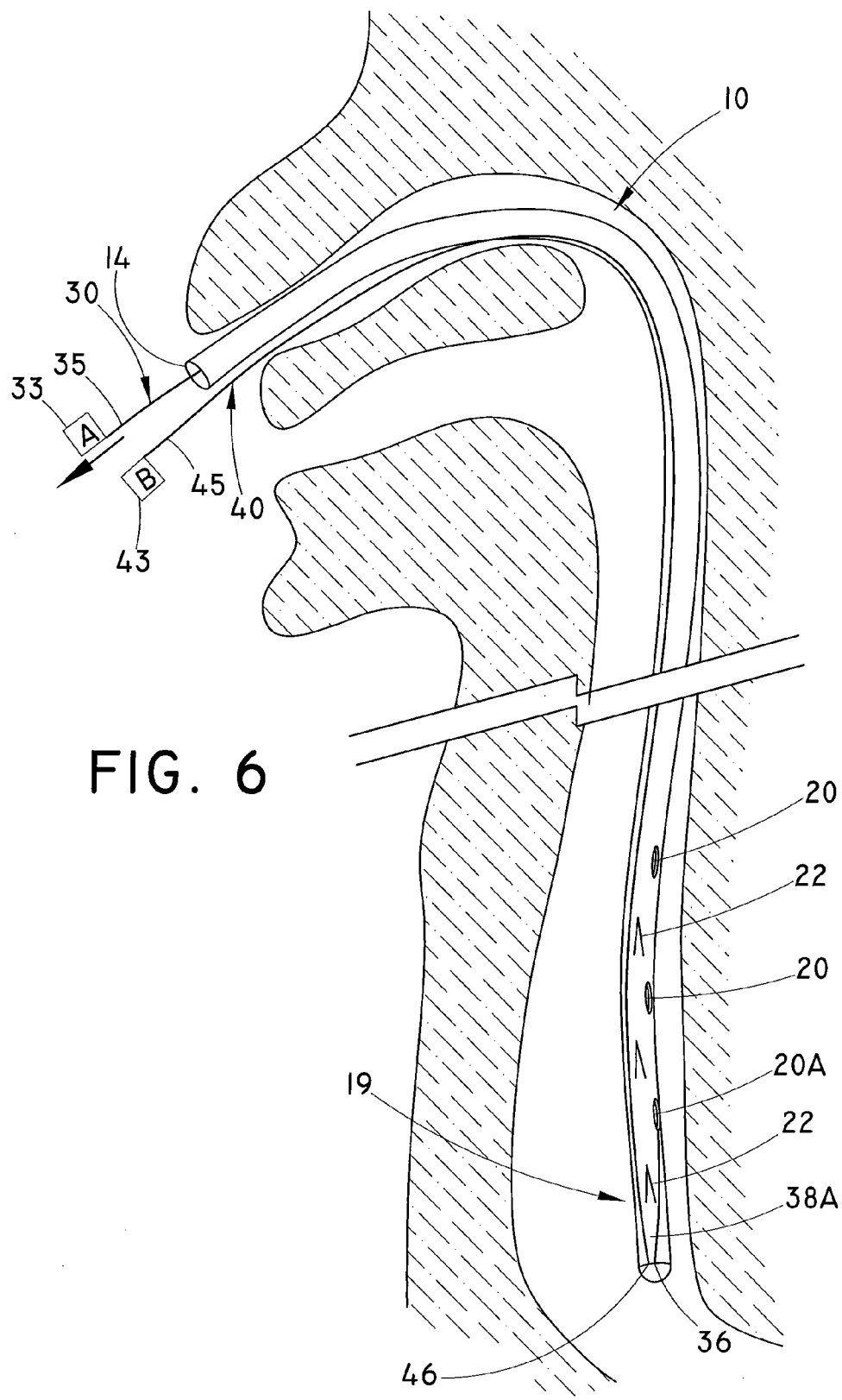
FIG. 6 illustrates the feeding tube once the distal end has been advanced into the jejunum of the patient by peristalsis.

FIG. 6 illustrates a feeding tube 10 that has been introduced nasally into the GI tract. Tube distal portion 19 has been advanced into the jejunum via peristalsis. Following introduction into the jejunum, the feeding tube is maintained in position for a period of time sufficient to carry out its desired function, e.g., the transmission of nutritional products to the patient.

When the operator determines that it is time to remove the feeding tube, Tab 33 (marked "A" in FIG. 6) affixed to the first string member 30 is pulled in the proximal direction (indicated by the arrow). This action causes tube distal end 18 to be folded backward, such that distal end 18 points in a proximal direction. This manipulation of the tube is shown in FIG. 5. For clarity, the GI tract and the jejunum have been omitted from the view of feeding tube 10 of FIG. 5, so that this initial manipulation of the feeding tube may be more easily observed. When feeding tube 10 has been adjusted to the position shown in FIG. 5, or in other words has been adjusted such that the distal tip 18 points in the proximal direction as shown, the tube is ready for withdrawal.

Figure 7:
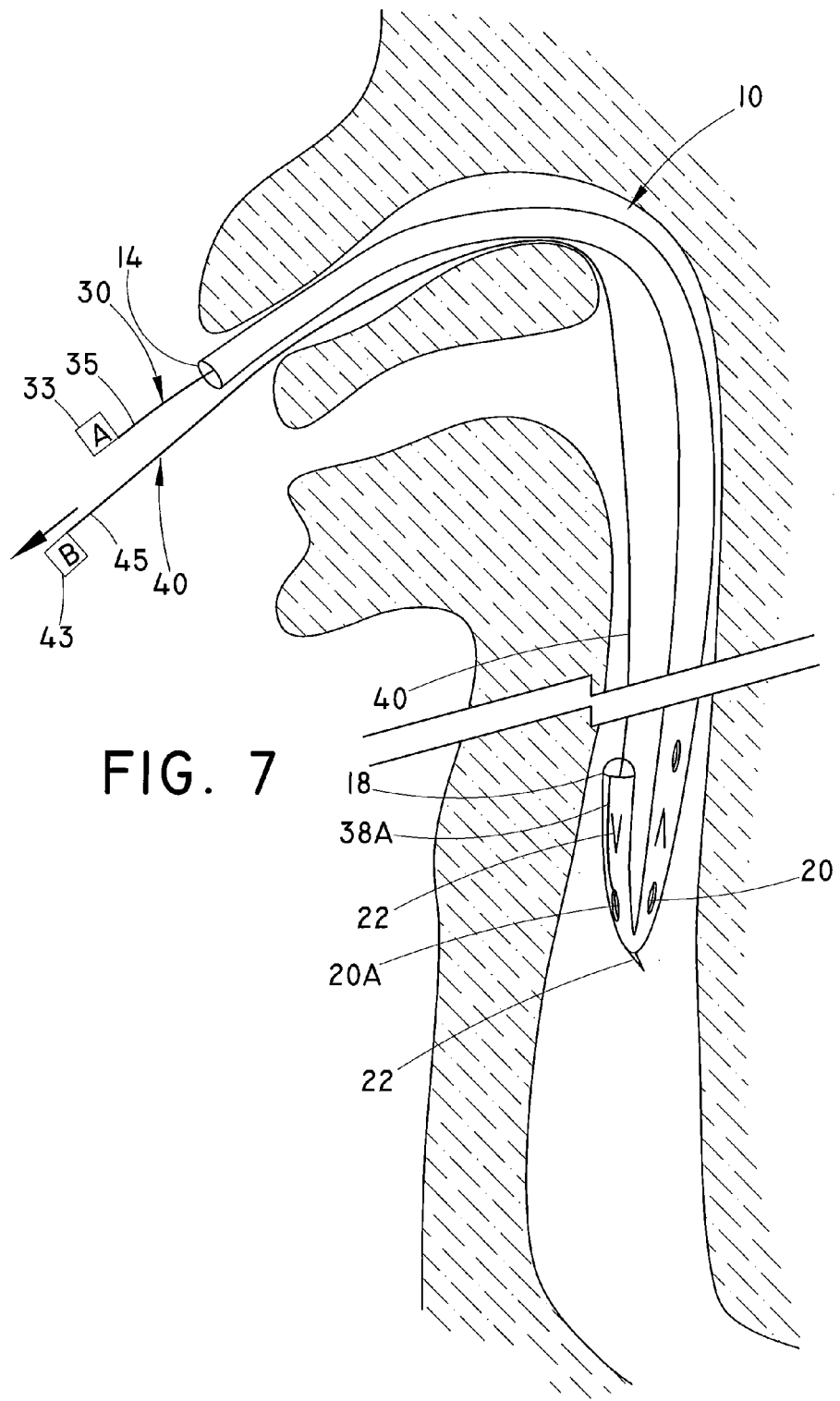
FIG. 7 illustrates the feeding tube wherein a length of the tube has been folded back on itself as it is being withdrawn from the gastrointestinal tract.

At this time, Tab 43 (marked "B") affixed to the second string member 40 is pulled in the proximal direction, and the force previously exerted on Tab 33 is released. The force on Tab 43 is maintained, which continued exertion causes the feeding tube to fold back upon itself as the distal end 18 is withdrawn through the GI tract, as shown in FIG. 7. Upon withdrawal, the tension on Tab 43 can generally be relaxed at any point between the time that the folded-back tube distal end 18 enters the stomach, and the time that distal end 18 has advanced In the proximal direction to a position just below the mouth.

Figure 8:
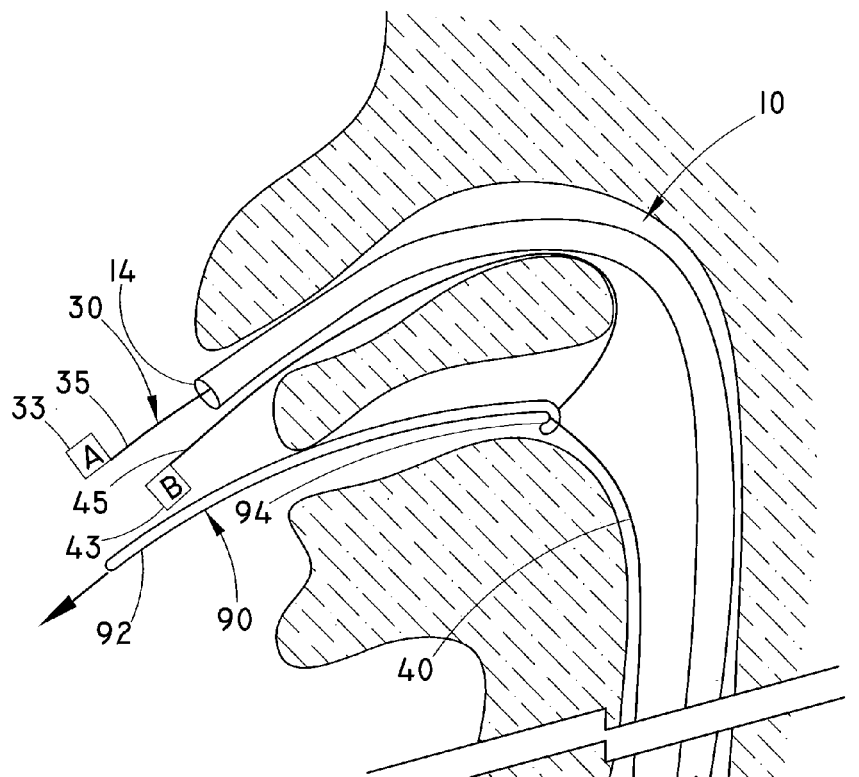
FIG. 8 illustrates the insertion of a hook member through the mouth of the patient to capture a string member of the feeding tube during withdrawal of the feeding tube.
Figure 11:
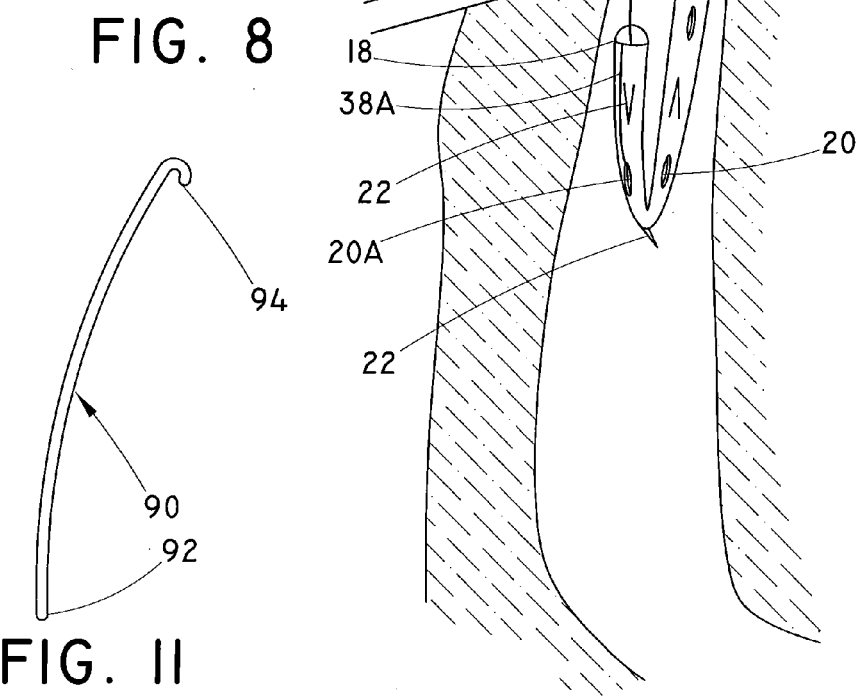
FIG. 11 illustrates the snare of FIGS. 8 and 9.

A snare 90 is inserted through the mouth and advanced along the throat to capture second string member 40 that runs along the exterior of elongated tubular member 12, as shown in FIG. 8. One example of a suitable snare is shown in FIG. 11. Snare 90 includes a shaft 92 with hook 94 at the distal end thereof. Shaft 92 may be linear or may have a slight curvature along its length. Typically, snare 90 is made from a plastic, metal, or metal alloy that is fabricated by known means to have a shape similar to that shown. Hook 94 may be integral with shaft 92, or may be securely affixed to the distal end of the shaft by conventional means. Since the function of snare 90 is merely to capture string member 40, those skilled in the art will appreciate that other devices capable of insertion through the mouth for capturing string member 40 may be substituted.

Figure 9:
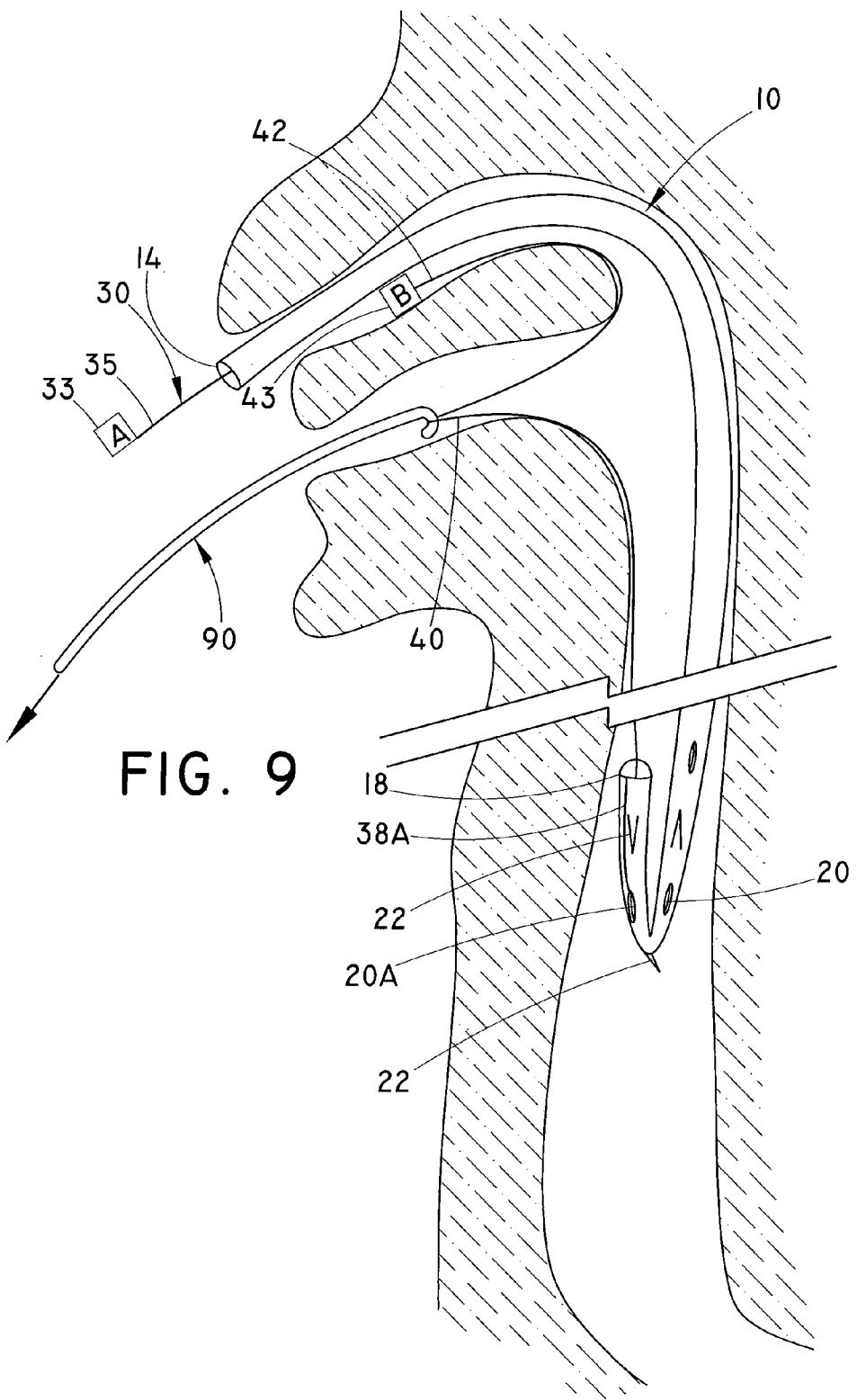
FIG. 9 illustrates a retraction of the hook member and string member from the mouth.
Figure 10:
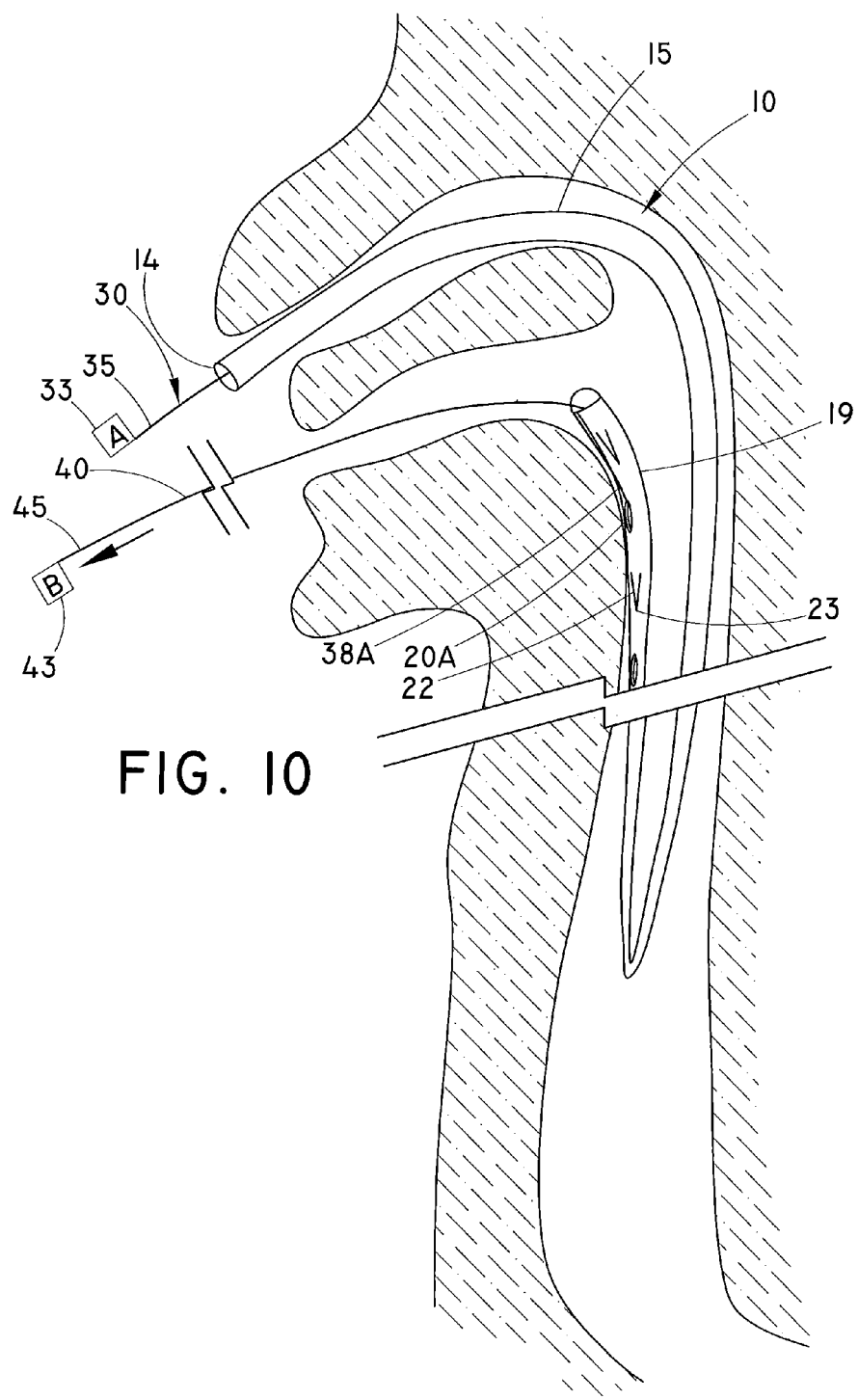
FIG. 10 illustrates withdrawal of the feeding tube through the mouth of the patent.

Once string member 40 has been captured as shown in FIG. 8, snare 90 is withdrawn from the mouth, as shown by the arrow in FIGS. 8 and 9. As a result, a proximal portion of the captured string member 40 is also withdrawn (FIG. 9), whereby string member proximal end 42 passes through the nasal cavity and out the oral cavity (mouth), such that it is accessible to the operator, as shown in FIG. 10. Tab 43 is then pulled in the direction of the arrow in FIG. 10 until the feeding tube is fully withdrawn through the mouth. As is evident in FIG. 10, since tips 23 of fins 22 point in the distal direction (since the distal end of the tube has been folded back upon itself), little or no trauma is experienced by the patient upon withdrawal. The fins merely fold or otherwise deflect inwardly during withdrawal if contact is made with interior surfaces of the body canal (e.g., the gastrointestinal tract).

Those skilled in the art will appreciate that although the tubular medical device described herein has been primarily referred to as a feeding tube, that additional uses may be made. For example, in addition to nutritional products, the tubular device may be used for delivering other fluids or fluid-like materials such as drugs, contrast materials and/or saline to target sites in the patient. The tubular device may also be used for delivery of specified materials to target sites in other body passageways. All such uses are considered within the scope of the invention.

Those skilled in the art will appreciate that the arrangement of the projections, such as the fins 22 described hereinabove, along the external surface of the elongated tubular member is merely one possible example. Numerous alternative configurations of projections, and arrangements of projections, may also be effective for the described purposes, all such arrangements and configurations being considered within the scope of the invention. Non-limiting examples of such projections include fins, flaps, mounds, bumps, etc., and combinations of the above. Such projections may be distributed along the external surface of the tubular member in a manner to promote ingress along an internal body pathway resulting from bodily contractions, as long as such projections are not arranged in a manner contrary to an objective recited herein of allowing withdrawal of the tube in non-traumatic fashion.

In addition to the foregoing, it is not necessary for the projections to be distributed along the surface of the distal end of tube 10 in the configuration described. Rather, in some cases, random, spiral, etc. configurations will be satisfactory. Since the purpose of the radial projections is to provide a grasping surface for the bodily contractions, a virtually unlimited number of arrangements could be fashioned to facilitate insertion of the tube via such contractions, the examples provided herein merely representing examples of preferred arrangements for a particular use.

It is therefore intended that the foregoing detailed description be regarded, as illustrative rather than limiting, and that it be understood that it is the following claims, including all equivalents, that are intended to define the spirit and scope of this invention.

What is claimed is:

1. A medical device configured for dynamic movement through a body passageway toward an interior target site, and for withdrawal therefrom, comprising:
   a generally flexible elongated tubular member having a proximal portion extending to a proximal end, a distal portion extending to a distal end, a plurality of projections disposed on an exterior surface of said distal portion, a lumen extending through said tubular member, and a port at said distal portion providing communication between said lumen and an environment of said body passageway exterior of the tubular member, said projections configured to engage an interior surface of the body passageway during bodily contractions thereof to promote ingress of the device along said body passageway in response to said contractions;
   a first string member having a proximal end and a distal end, said first string member extending interiorly of said tubular member along said lumen to said port, and exteriorly of said tubular member from said port substantially to said tubular member distal end, said first string member arranged such that said proximal end extends proximal of said tubular member proximal end, and said distal end is affixed to said tubular member distal of said port; and
   a second string member having a proximal end and a distal end, said second string member extending exteriorly along said tubular member substantially to said distal end of said tubular member, said second string member arranged such that said proximal end extends proximal of said tubular member proximal end, and said distal end is affixed to said tubular member distal of said port.

2. The medical device of claim 1, wherein said port at said distal portion comprises a first port, said tubular member further comprising a plurality of additional ports along said distal portion.

3. The medical device of claim 1, wherein said projections are configured to resist an unintended egress of the device.

4. The medical device of claim 1, wherein said first string member proximal end includes a graspable portion, said first string member and said tubular member aligned and configured such that upon exertion of a proximal pulling force on said first string member graspable portion, said tubular member distal end is flexed such that it points in a proximal direction.

5. The medical device of claim 4, wherein said second string member proximal end includes a graspable portion, said second string member aligned and configured relative to said flexed tubular member distal end such that upon exertion of a proximal pulling force on said second string member graspable portion, said tubular member distal end is removable from said body passageway.

6. The medical device of claim 1, comprising a snare member configured for capturing a proximal portion of said second string member, and for withdrawing said second string member proximal portion from a body opening prior to a withdrawal of said elongated tubular member from said body passageway.

7. The medical device of claim 6, wherein said snare comprises a generally elongated shaft having a hook member at a distal portion thereof for capturing said second string member proximal portion.

8. A feeding tube configured for dynamic movement through the gastrointestinal tract of a patient to the jejunum, and for withdrawal therefrom, comprising:
   a flexible elongated tubular member having a proximal portion extending to a proximal end, a distal portion extending to a distal end, a plurality of projections disposed along an exterior surface of said distal portion, a lumen extending through said tubular member, and a port at said distal portion providing communication between said lumen and the jejunum, said projections configured to engage an interior surface of the gastrointestinal tract during contractions thereof to promote ingress of the tubular member along the gastrointestinal tract to the jejunum in response to said contractions;
   a first string member having a proximal end and a distal end, said first string member extending interiorly of said tubular member along said lumen to said port, and exteriorly of said tubular member from said port to a first affixation point of said first string member distal end substantially at said tubular member distal end, said first string member proximal end extending proximal of said tubular member proximal end, said first string member configured and arranged relative to said tubular member such that upon exertion of a pulling force on said first string member proximal end, said tubular member distal portion flexes in a direction of said force; and
   a second string member having a proximal end and a distal end, said second string member extending exteriorly along said tubular member to a second affixation point of said second string member distal end substantially at said tubular member distal end, said second string member proximal end extending proximal of said tubular member proximal end, said second string member arranged such that upon exertion of a pulling force on said second string member proximal end, said tubular member is withdrawn from said gastrointestinal tract responsive to said force.

9. The feeding tube of claim 8, wherein said port at said distal portion comprises a first port, said tubular member further comprising a plurality of additional ports along said distal portion, said additional ports being configured for passage of a fluid material therethrough.

10. The feeding tube of device of claim 8, wherein said distal projections comprise a series of fins disposed along said exterior surface, said fins having respective fin tips and being aligned along said exterior surface such that said fin tips point in a direction away from the jejunum during ingress of the device.

11. The feeding tube of claim 10, wherein said tubular member is capable of being folded back along its length during egress of the device, and wherein said fin tips point in a direction toward the jejunum during egress.

12. The feeding tube of claim 8, wherein said distal projections are formed from said elongated tubular member.

13. The feeding tube of claim 8, wherein at least one of said string members includes a grasping member at the proximal end thereof.

14. The feeding tube of claim 13, wherein each of said string members includes a grasping member at the proximal end thereof, said grasping members comprising respective tabs, and wherein each of said tabs includes a designator for the respective string member.

15. The feeding tube of claim 8, wherein said string members include identifying indicia such that each said string member is visually distinguishable from the other string member.

16. The feeding tube of claim 8, in combination with a snare member configured for capturing a proximal portion of said second string member, and for withdrawing said second string member proximal portion through a body opening prior to a withdrawal of said elongated tubular member from the gastrointestinal tract.

17. A method for insertion of a feeding tube into the jejunum of a patient, and withdrawal therefrom, comprising:

inserting a distal end of a feeding tube nasally into the gastrointestinal tract of the patient, the feeding tube having a proximal portion extending to a proximal end, a distal portion extending to the distal end, a plurality of projections disposed along an exterior surface of the distal portion, a lumen extending through the feeding tube, and a port at the distal portion, the feeding tube including a first string member and a second string member, the first string member extending interiorly of said feeding tube along the lumen to the port, and exteriorly of the feeding tube from the port to a first affixation point substantially at the feeding tube distal end, the first string member having a proximal end extending proximal of the feeding tube proximal end, the second string member extending exteriorly along said feeding tube to a second affixation point substantially at the feeding tube distal end, the second string member having a proximal end extending proximal of the feeding tube proximal end;

advancing the feeding tube along the gastrointestinal tract by peristaltic contractions acting upon the feeding tube projections, such that the distal portion of the feeding tube advances into the jejunum;

exerting a pulling force on the proximal end of the first string member such that the feeding tube distal portion flexes in a direction of said pulling force;

exerting a pulling force an the proximal end of the second string member and withdrawing said feeding tube distal portion a distance along the gastrointestinal tract, such that a length of said feeding tube distal portion folds back upon a remaining length of the feeding tube;

orally inserting a snare to capture a proximal portion of the second string member, and withdrawing said snare and the proximal end of the second string member through the mouth of the patient; and exerting a pulling force on the second string member to withdraw the feeding tube through the mouth of the patient.

18. The method of claim 17, wherein said snare comprises an elongated shaft having a hook member at a distal portion thereof, said hook member configured to capture the second string member and to withdraw said second string member through the mouth of the patient.

19. The method of claim 17, wherein said projections comprise a series of fins disposed along said exterior surface, said fins having respective fin tips and being aligned along said exterior surface such that said fin tips point in a direction away from the jejunum during said advancing of said feeding tube, and said fin tips point in a direction toward the jejunum during withdrawal of said feeding tube.

20. The method of claim 19, wherein each of said string members includes a grasping member at the proximal end thereof, and wherein at least one of said grasping members includes a designator for the at least one string member.

* * * * *